United States Patent

Shum et al.

Patent Number: 5,486,641

Date of Patent: Jan. 23, 1996

[54] SOLVENT-FREE PROCESS FOR THE PREPARATION OF THE BETA CRYSTALLINE MODIFICATION OF 2,2',2''-NITRILO[TRIETHYL-TRIS-(3,3',5,5',-TETRA-TERT-BUTYL-1,1'-BIPHENYL-2,2'-DIYL) PHOSPHITE]

[75] Inventors: Sai P. Shum, Pleasantville, N.Y.; Stephen D. Pastor, Danbury, Conn.

[73] Assignee: Ciba-Geigy Corporation, Tarrytown, N.Y.

[21] Appl. No.: 396,315

[22] Filed: Feb. 28, 1995

[51] Int. Cl.[6] .................................................. C07F 9/6574
[52] U.S. Cl. .................................................. 558/78; 524/119
[58] Field of Search .................................................. 558/78

[56] References Cited

U.S. PATENT DOCUMENTS

| 4,318,845 | 3/1982 | Spivack et al. |
| 4,374,219 | 2/1983 | Spivack et al. |
| 5,276,067 | 1/1994 | Pastor et al. |
| 5,326,802 | 7/1994 | Pastor et al. |
| 5,331,031 | 7/1994 | Pastor et al. |
| 5,334,739 | 8/1994 | Pastor et al. |
| 5,344,860 | 9/1994 | Pastor et al. |
| 5,373,040 | 12/1994 | Pastor et al. |

*Primary Examiner*—Robert W. Ramsuer
*Assistant Examiner*—Michael G. Ambrose
*Attorney, Agent, or Firm*—Luther A. R. Hall

[57] ABSTRACT

The beta crystalline form of 2,2',2''-nitrilo[triethyl-tris-(3,3',5,5'-tetra-tert-butyl-1,1'-biphenyl-2,2'-diyl) phosphite] is obtained by the thermal treatment of the phosphite compound at 125° C. in the absence of any solvent.

The beta crystalline form is an effective process stabilizer for polyolefins, particularly polypropylene.

4 Claims, No Drawings

SOLVENT-FREE PROCESS FOR THE PREPARATION OF THE BETA CRYSTALLINE MODIFICATION OF 2,2',2"-NITRILO[ TRIETHYL-TRIS-(3,3',5,5',-TETRA-TERT-BUTYL-1,1'-BIPHENYL-2,2'-DIYL) PHOSPHITE]

The instant invention is to a novel process to prepare the beta, triclinic crystalline form of 2,2',2"-nitrilo[triethyl-tris-(3,3',5,5'-tetra-tert-butyl-1,1'-biphenyl-2,2'-diyl) phosphite].

BACKGROUND OF THE INVENTION 2,2',2"-Nitrilo[triethyl-tris-(3,3',5,5'-tetra-tert-butyl-1,1'-biphenyl-2,2'-diyl) phosphite] is a compound having the formula I

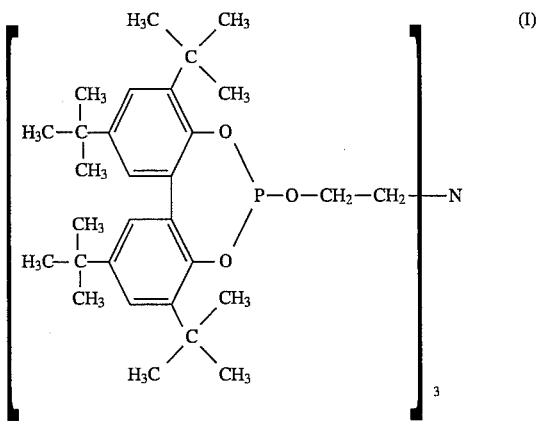

This compound of formula I is useful as a processing stabilizer for organic polymers as taught in U.S. Pat. Nos. 4,318,845 and 4,374,219. It has been found that the compound can exist in a number of crystalline forms as well as an amorphous form. These forms of the compound of formula I are described in U.S. Pat. No. 5,276,076; 5,326,802; 5,331,031; 5,334,739; 5,344,860 and 5,373,040. These different forms of the compound of formula I exhibit acceptable properties in respect to handling, apparent density, flowability, meterability, storage stability, hydrolytic stability and better migration into polymeric substrates.

The beta, triclinic crystalline form is specifically described in U.S. Pat. Nos. 5,326,802 and 5,344,860. These patents describe the process of making the beta form by solvent crystallization or by melt crystallization. Both prior art processes require solvents or high temperature in addition to an extended crystallization time. The present invention pertains to a process for a solvent-free and time saving crystallization leading to the instant beta, triclinic form of the compound of formula I.

DETAILED DISCLOSURE

The instant invention pertains to a process for the preparation of the beta, triclinic form of the compound of formula I

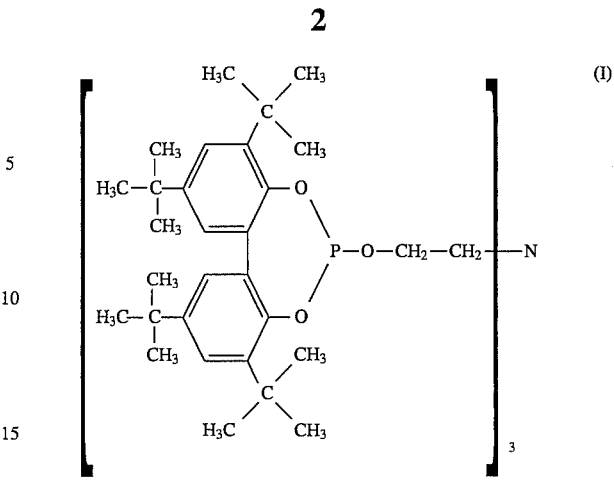

characterized by melting in the range of 200°–207° C. and by an X-ray diffraction pattern exhibiting lines of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27, 27.7, 28.4 and a relative absolute configuration of the three stereo axes of the dibenzo[d,f][1,3,2]dioxaphosphepin rings of R*,R*,S*, which comprises placing the compound of formula I in a closed vessel and heating the vessel at atmospheric pressure to 90°–160° C. for 10–20 minutes to convert the starting compound into a crystalline mass which is the instant beta, triclinic crystalline form of the compound of formula I.

Preferably, the compound of formula I is heated at 120°–130° C. (most preferably at 125° C.) for 15 minutes to convert it into the beta, triclinic form.

Differential scanning calorimetry (DSC) measurements are obtained on a TA Instrument Inc., 910 differential scanning calorimeter, with a 100 mL/min nitrogen purge, aligned aluminum pan, temperature scan at 5° C./min to 230° C.

X-ray diffraction patterns are recorded on a Philips Norelco X-ray Diffractometer unit, using Cu-Kα radiation with a nickel filter.

EXAMPLE 1

The compound of formula I, 2,2',2"-nitrilo[triethyl-tris-(3,3',5,5'-tetra-tert-butyl -1,1'-biphenyl-2,2'-diyl)phosphite], is prepared according to procedure of Example 4 of U.S. Pat. No. 4,318,845. Five grams of the product obtained is placed in a 20 mL vial with a screw cap. The vial is then placed in an oven at ambient atmospheric pressure at 125° C. for fifteen minutes. The crystalline mass which forms is then ground into a white powder which is the beta, triclinic crystalline form of the compound of formula I, having a melting point of 205° C. (the melting point is determined by differential scanning calorimetry and the peak temperature in the endotherm is recorded as the melting point).

An X-ray diffraction pattern obtained using Cu-Kα exhibits diffraction angles (2θ) confirming that the powder obtained is the beta, triclinic crystalline form of the compound of formula I.

EXAMPLE 2

The compound of formula I is prepared according to the procedure of Example 4 of U.S. Pat. No. 4,318,845.

In order to compare the instant process with the process disclosed in U.S. Pat. No. 5,326,802 for making the beta crystalline form, equal quantities of the compound of formula I prepared above are subjected to the instant process and to the prior art process as seen in the table below.

| Process | Temperature | Time |
| --- | --- | --- |
| Melt Crystallization | 180° C. | 16 hours |
| Instant | 125° C. | 15 minutes |
| Instant | 160° C. | 15 minutes |

Both processes lead to the formation of the beta, triclinic crystalline form of the compound of formula I, but it is clear that the instant process provides a much faster and more economic (lower temperature) way to prepare the instant beta, triclinic crystalline form of the compound of formula I.

What is claimed is:

1. A process for the preparation of the beta, triclinic form of the compound of formula I

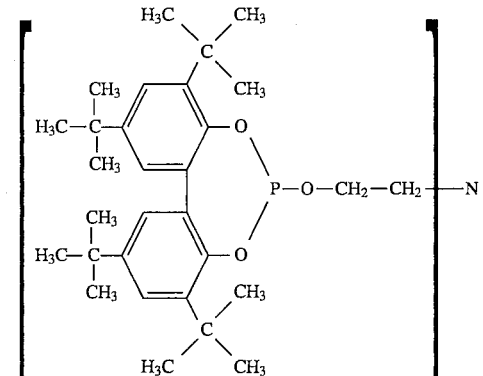

characterized by melting in the range of 200°–207° C. and by an X-ray diffraction pattern exhibiting lines of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7, 28.4 and a relative absolute configuration of the three stereo axes of the dibenzo[d,f][1,3,2]dioxaphosphepin rings of R*,R*,S*, which comprises placing the compound of formula I in a closed vessel and heating the vessel at atmospheric pressure to 90°–160° C. for 10–20 minutes to convert the starting compound into a crystalline mass which is the beta, triclinic crystalline form of the compound of formula I.

2. A process according to claim 1 wherein the temperature is 120°–130° C.

3. A process according to claim 2 wherein the temperature is 125° C.

4. A process according to claim 1 wherein the vessel is heated for 15 minutes.

* * * * *